United States Patent

Emig et al.

[11] 4,065,501
[45] Dec. 27, 1977

[54] BASIC ENOL ETHER AND ACID ADDITION SALTS THEREOF

[75] Inventors: Peter Emig; Hans Pohle, both of Brackwede; Gerhard Scheffler, Senne; Norbert Brock, Uerentrup; Hans-Dieter Lenke, Ludwigshafen; Jorg Pohl, Halle, all of Germany

[73] Assignee: Asta-Werke Aktiengesellschaft, Brackwede, Germany

[21] Appl. No.: 557,535

[22] Filed: Mar. 12, 1975

[30] Foreign Application Priority Data

Mar. 22, 1974 Germany .............................. 2413814

[51] Int. Cl.² .............................................. C07C 91/16
[52] U.S. Cl. ........................... 260/570.6; 260/296 AE; 260/325 AM; 260/501.18; 260/501.19; 260/611 A; 424/248.57; 424/267; 424/274; 424/316; 424/325; 424/330; 544/106
[58] Field of Search ............ 260/570.6, 501.18, 501.19

[56] References Cited

U.S. PATENT DOCUMENTS

| | | | |
|---|---|---|---|
| 2,397,799 | 4/1946 | Martin et al. | 260/570.6 |
| 2,762,812 | 9/1956 | Archer et al. | 260/570.5 X |
| 3,282,937 | 11/1966 | Klavehn et al. | 260/570.5 X |
| 3,308,159 | 3/1967 | Doebel | 260/570.5 |
| 3,553,225 | 1/1971 | Kaiser et al. | 260/570.6 |
| 3,686,311 | 8/1972 | Arnold et al. | 260/570.6 |

*Primary Examiner*—Robert V. Hines
*Attorney, Agent, or Firm*—McNenny, Pearne, Gordon, Gail, Dickinson & Schiller

[57] ABSTRACT

The present invention is related to new basic enol ethers having the general formula

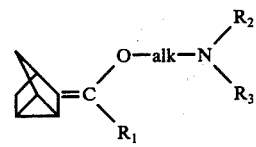

and to the pharmacologically acceptable acid addition salts thereof. The invention is further related to process for the treatment of spasmodic conditions in humans by administering a compound of the above general formula or a pharmacologically acceptable acid addition salt thereof to a human suffering from such conditions.

4 Claims, No Drawings

BASIC ENOL ETHER AND ACID ADDITION SALTS THEREOF

This invention relates to new basic enol ethers and to their pharmacologically acceptable acid addition salt. The invention further relates to pharmaceutical compositions containing the new compounds as active principle.

The compounds according to the invention correspond to the following general formula:

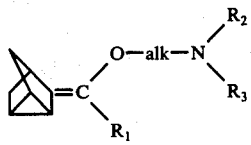

wherein
- $R_1$ represents a member selected from the group consisting of the unsubstituted phenyl, pyridyl and thienyl group and such groups (preferably the phenyl group) substituted by members selected from the group consisting of halogen (preferably bromine, chlorine and fluorine, most preferably chlorine), lower alkyl having from 1 to 4 carbon atoms, nitro,
- trifluoromethyl, hydroxy and lower alkoxy having from 1 to 4 carbon atoms, alk represents a member selected from the group consisting of the linear and branched alkylene groups having from
- 2 to 4 carbon atoms, and
- $R_2$ and $R_3$, which may be the same or different, represent members selected from the group consisting of hydrogen, alkyl having from 1 to 4 carbon atoms and,
- $R_2$ and $R_3$ together, an alpha, omega-polymethylene group containing from 4 to 5 methylene groups and the polymethylene group containing 4 methylene groups and an oxygen in the chain symmetrically positioned therein.

Of the compounds corresponding to general formula I, those are preferred wherein $R_1$ represents a member selected from the group consisting of the unsubstituted phenyl group and the phenyl group monosubstituted in the ortho position as already indicated, alk has the same meaning as above indicated and most preferably represents the ethylene group, and $R_2$ and $R_3$ which may be the same or different, represent a member selected from the group consisting of hydrogen and the alkyl groups having from 1 to 4 carbon atoms, most preferably both $R_2$ and $R_3$ representing the ethyl group.

Suitable acid addition salts are, in particular, those of hydrochloric acid, sulphuric acid, phosphoric acid, acetic acid, glycolic acid, lactic acid, maleic acid, succinic acid, tartaric acid, citric acid, benzoic acid, malic acid, β-hydroxy naphthoic acid and embonic acid.

The compounds of general formula I may be prepared by one of the following methods:

A. A compound corresponding to the general formula

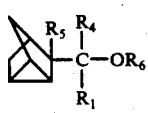

in which
- $R_1$ has the same meaning as in formula I and either $R_4$ and $R_5$ together represent a bond and $R_6$ represents Me, or
- $R_4$ represents as separable group such as —C≡CH, —CH$_2$SOCH$_3$, —CN or —CH$_2$NO$_2$, and $R_5$ and $R_6$ represent hydrogen atoms, is reacted with a compound corresponding to the general formula

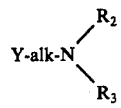

in which
- Y is a halogen atom or a sulphonic acid ester group, and alk, $R_2$ and $R_3$ have the same meaning as in formula I, at room temperature or at elevated temperature in a suitable solvent and in the presence of a basic condensation agent,
- Me in formula II being the cation of the basic condensation agent used, or B. a compound corresponding to the general formula

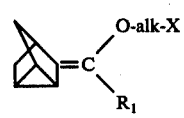

in which
- X is a chlorine or bromine atom and
- $R_1$ and alk have the same meaning as in formula I, is reacted with a compound corresponding to the general formula

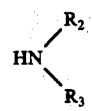

in which
- $R_2$ and $R_3$ have the same meaning as in formula I, in the presence of an acid-binding agent at room temperature or elevated temperature and under normal or elevated pressure in a suitable solvent, or C. a compound corresponding to the general formula

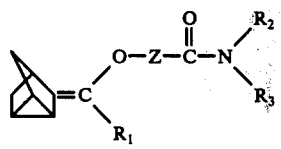

in which
- $R_1$, $R_2$ and $R_3$ have the same meaning as in formula I, and Z is a linear or branched alkylene group with 1 to 3 carbon atoms, is reacted with a complex metal hydride, preferably with lithium aluminium hydride, in a suitable inert solvent either at room temperature or at elevated temperature, or D. a compound corresponding to the general formula

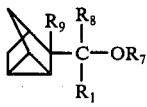
(VII)

in which
R$_7$ is a lower alkyl group with 1 to 4 carbon atoms and
R$_8$ and R$_9$ together represent a bond or
R$_9$ is a hydrogen atom and
R$_8$ is a lower alkoxy group with 1 to 4 carbon atoms and
R$_1$ has the same meaning as in formula I, is reacted with a compound corresponding to the general formula

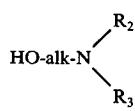
(VIII)

in which
alk, R$_2$ and R$_3$ have the same meaning as in formula I, in the presence of an acid catalyst at room temperature or elevated temperature and in the presence or absence of an organic solvent.

The basic condensation agent used in the methods described above is, for example, sodium hydride, sodium amide, sodium oxide, sodium or potassium hydroxide or alcoholate or potassium tert.-butylate.

Suitable acid-binding agents are tertiary aliphatic and aromatic organic amines and N-containing heterocycles, although it is preferred to use an excess of the amines of general formula V used for the reaction itself.

Preferred acid catalysts are hydrochloric acid, sulphuric acid, phosphoric acid and p-toluene sulphonic acid. Suitable organic solvents are benzene, toluene and xylene, dioxan, tetrahydrofuran and diethyl ether, alcohols such as methanol, ethanol and isopropanol, also chlorinated organic solvents such as methylene chloride, chloroform, 1,2-dichloroethane and chlorobenzene, as well as dipolar aprotic solvents such as dimethyl formamide, dimethyl acetamide, N-methyl pyrrolidone and dimethyl sulphoxide or mixtures thereof.

Preferred solvents for method A) are benzene, toluene, xylene and the dipolar aprotic solvents, preferred solvents for method B), in addition to those mentioned in reference to method A), are alcohols such as methanol, ethanol and isopropanol, preferred solvents for method C) are diethyl ether, tetrahydrofuran and dioxan, and preferred solvents for method D) are chlorinated organic solvents such as methylene chloride, chloroform, 1,2-dichloroethane and chlorobenzene.

The methods according to the invention are carried out at temperatures in the range from 0° to 150° C under normal pressure or elevated pressure. However, method B) is preferably carried out at temperatures between 40° and 140° C under elevated pressure, optionally in an autoclave, whereas the other methods are preferably carried out under normal pressure at temperatures between 15° C and the boiling temperature of the solvent.

The basic enol ethers of general formula I prepared by the methods described above are cis-trans isomers which may optionally be separated.

The compounds according to the invention may be converted into their acid addition salts by the usual methods, or the free bases or other salts may be prepared from the acid addition salts obtained by the usual methods.

The compounds of general formula I and their acid addition salts have valuable pharmacological properties. Above all, they are effective spasmolytics, although they also show anti-allergic, anti-depressive and tremor-inhibiting activity. Their spasmolytic acitivity was tested in situ by the method reported by N. BROCK, D. LORENZ and H. BARTLING in Arch. Ex. Path. Pharmacol. 215, 512 – 524 (1952) where the active compound is injected intravenously into the small intestine of guinea pigs. The DE 75 is the dose which reduces by 75% the spasms caused by neostigmine or barium chloride. For example, the substances of Examples 3 and 18 are considerably more effective than the standard substances Camylofin and papaverine. The myotropic spasmolytic activity of Camylofin (BaCl$_2$-induced spasm) is exceeded by the factor seven by the compound of Example 3 and by the factor eleven by the compound of Example 18. The neurotropic spasmolytic activity of Camylofin (neostigmine-induced spasm) is exceeded by the factor two by the compound of Example 3 and by the factor six by the compound of Example 18. In the model test, papaverine is only active in higher subtoxic doses (serious breathing difficulties).

The pharmacological properties are set out in Table 1 below:

Table 1

| Spasmolytic activity | neostigmine spasm | | | | BaCl$_2$ - spasm | | | |
|---|---|---|---|---|---|---|---|---|
| | DE 75 | | relative activity based on Camylofin = 1.0 | | DE 75 | | relative activity based on Camylofin = 1.0 | |
| Preparation | mg/kg. | μmol/kg. | mg/kg. | μmol/kg. | mg/kg. | μmol/kg. | mg/kg. | μmol/kg. |
| Compound of Example 3 | 2.11 | 7.09 | 1.94 | 1.47 | 1.04 | 3.49 | 7.02 | 5.33 |
| Compound of Example 18 | 0.683 | 2.19 | 6.00 | 4.75 | 0.685 | 2.20 | 10.66 | 8.45 |
| papaverine | 18.9 | 55.8 | 0.22 | 0.186 | 26.0 | 69.0 | 0.28 | 0.27 |
| Camylofin | 4.1 | 10.4 | 1.00 | 1.00 | 7.3 | 18.6 | 1.00 | 1.00 |

On the basis of the degree to which the spontaneous colon peristalsis of non-anaesthetized dogs is suppressed, the compound of Example 3 administered intravenously is 8.4 times more active than Camylofin. An enteral activity of 9.2% can be calculated from the quotient of the active doses after intravenous and enteral administration. In addition to the significant increase in spasmolytic activity, there is an appreciable reduction in systemic side effects based on the neurotropic activity component. Neither the intravenous application nor the enteral application of spasmolytically active doses produced the least sign of mydriasis in non-anaesthetized dogs. A moderate increase in heart rate after intravenous administration, of which the trend corresponds to the spasmolytic effect in the case of Camylofin and also in the case of all other commercial spasmolytics, disappears again after only 2 minutes in the case of the compound of Example 3 and is in no way related to blocking of the colon peristalsis which lasts for more than 30 minutes. Accordingly, this compound achieves a hitherto unknown organ specificity in its spasmolytic effect. Hence this compound is particularly preferred.

The toxic doses of the compound of Example 3 are somewhat higher than those of Camylofin in rats, mice and dogs, irrespective of the method of administration. The approximately 10% reduction in toxicity and the more than 8-fold increase in activity give this compound a therapeutic index which is greater by about the factor ten than that of the standard substance Camylofin.

In the case of the compound of Example 18, the toxic doses are somewhat lower than in the case of Camylofin. However, in view of the significant increase in spasmolytic activity on the ileum of guinea pigs, its therapeutic index is once again greater by about the factor seven.

Table 2

Acute toxicity in mice (DL 50 [mg/kg]) with intravenous administration

| Compound of Example No. | DL 50 [mg./kg.] |
|---|---|
| 3 | 40.7 |
| 18 | 30.3 |
| Camylofin | 36.2 |

The compounds of the present invention are most useful in the treatment of spasmodic conditions in humans, in particular such conditions of the abdominal viscera such as colics of the biliary and urinary tracts, tenesmic attacks of the bladder, ulcer pain, dysmenorrheas or for the easing of labors. The compounds are administered orally or intraperitoneally in usual forms such as dragees, tablets, suppositories or injection solutions in daily doses ranging from 5 to 60 mg, of the base compound or the equivalent amount of a suitable acid addition salt thereof, with 5 to 10 mg. of the base or the equivalent amount of a salt as single dose. For instance 1 to 2 tablets containing 10 mg. of the base or the equivalent amount of a salt are administered 2 to 3 times a day or 1 to 2 ml. of an injection solution containing 10 mg./2 ml. of the base or the equivalent amount of a salt are slowly injected intravenously or intramuscularly.

The invention is illustrated by the following Examples without however limiting the same thereto.

EXAMPLE 1

N,N-Dimethyl-N-{2-[α-(tricyclo(2.2.1.0$^{2.6}$)hept-3-ylidene)-benzyloxy]-ethyl}-amine A suspension of 3.9 g. (0.1 mol) of sodium amide in 45 ml of anhydrous toluene was heated to boiling point, followed by the dropwise addition with stirring of a solution of 19.83 g. (0.1 mol) of tricyclo-(2.2.1.0$^{2.6}$)hept-3-yl phenyl ketone and 10.76 g. (0.1 mol) of β-dimethy amino ethyl chloride in 85 ml. of anhydrous toluene. After stirring at reflux temperature for 1.5 hours, the mixture was cooled to room temperature and 30 ml. of water added to destroy the sodium amide. The organic phase was then separated off, washed three times with 30 ml. of water, dried over anhydrous sodium sulphate and concentrated in vacuo. The crude base left was dissolved while cooling with ice in a mixture of 9.85 g. (0.1 mol) of 37% hydrochloric acid in 60 ml. of water, after which the aqueous solution was extracted three times with 30 ml. of ether, the aqueous phase separated off and a solution of 10 ml. of 10N sodium hydroxide in 20 ml. of ice water added dropwise to it while cooling. The mixture was extracted with a total of 150 ml. of ether, the ether phase was dried over anhydrous sodium sulphate, the inorganic salt filtered off and the product concentrated in vacuo. The crude base obtained was purified through an aluminium oxide column, followed by fractionation in a high vacuum.

BP$_{0.002}$: 107° - 115° C. Yield: 20.5 g. (76% of the theoretical) Hydrochloride: Mp: 168° - 171° C. (from ethyl acetate/isopropanol

EXAMPLE 2

N-Ethyl-N-{2-[α-(tricyclo(2.2.1.0$^{2.6}$)hept-3-ylidene)-benzyloxy]-ethyl}-amine A solution of 90 g. (0.345 mol) of β-chloroethyl-{α-[tricyclo-(2.2.1.0$^{2.6}$)hept-3-ylidene]-benzyl}-ether and 69 g. (1.53 mol) of ethylamine in 250 ml. of anhydrous benzene was heated for 5 hours to 140° C. in a 1 liter capacity autoclave. After cooling, the ethylamine hydrochloride was filtered off under suction, the mother liquor concentrated in vacuo and the residue subjected to acid-alkaline working up. The basic fraction was fractionated in vacuo.

Bp 0.08: 130° 14 134° C. Hydrochloride: Mp. 185° - 186° C.

EXAMPLE 3

N,N-Diethyl-N-{2-[α-(tricyclo-(2.2.1.0$^{2.6}$)hept-3-ylidene)-benzyloxy]-ethyl}-amine A suspension of 46.8 g. (1.2 mol) of sodium amide in 450 ml. of anhydrous toluene was heated to boiling point, followed by the dropwise addition with stirring of a solution of 198.3 g. (1 mol) of tricyclo-(2.2.1.0$^{2.6}$)hept-3-yl phenyl ketone and 162.7 g. (1.2 mol) of β-diethyl amino ethyl chloride in 850 ml. of anhydrous toluene. After stirring at reflux temperature for 1 hour, the reaction mixture was cooled to room temperature and 300 ml. of water added dropwise to destroy the sodium amide. The organic phase was then separated off, washed three times with 300 ml. of water, dried over anhydrous sodium sulphate and concentrated in vacuo. The crude base left was dissolved while cooling with ice in a mixture of 110 g. of 37% hydrochloric acid and 900 ml. of water, after which the aqueous solution was extracted twice with 400 ml. of ether, the aqueous phase separated off and extracted three times with 800 ml. of chloroform. The combined chloroform extracts were washed with 800 ml. of water and dried over anhydrous sodium sulphate. After filtration, the chloroform solution was concentrated by evaporation in vacuo. The residue was dissolved in 500 ml. of water, a solution of 60 g. of sodium hydroxide in 100 ml. of water added while cooling with ice and the mixture extracted with a total of 1 liter of peroxide-free ether. The ether phase was dried with anhydrous sodium sulphate, concentrated by evaporation in vacuo and the residue left fractionated.

Bp 0.1: 140° – 145° C. Yield: 243 g. (81.7% of the theorezical). Hydrochloride: To prepare the hydrochloride, the base was dissolved in anhydrous ether, and somewhat less than the theoretical quantity of anhydrous HCl-containing ether added with vigorous stirring and cooling with ice. The hydrochloride precipitated was filtered off under suction, washed with anhydrous ether and recrystallized from ethyl acetate.

Mp: 127° C.

Hydrogen fumarate: To prepare the hydrogen fumarate, the base was dissolved in isopropanol and the theoretical quantity of fumaric acid in a little isopropanol added with vigorous stirring and cooling with ice. The salt which crystallized after only a short time was filtered off under suction and purified with anhydrous ether.

Mp: 123° – 126° C. (from isopropanol).

EXAMPLE 4

N,N-Diethyl-N-{-2-[α-tricyclo-(2.2.1.0$^{2,6}$)hept-3-ylidene)-benzyloxy]-ethyl}-amine A solution of 99.2 g. (0.5 mol) of tricyclo-(2.2.1.0$^{2,6}$) hept-3-yl phenyl ketone in 150 ml. of anhydrous toluene was added to a suspension of 18 g. (0.6 mol) of sodium hydride (80% in mineral oil) in 200 ml. of anhydrous toluene. After heating for 1 hour to 70° C., the reaction mixture was cooled to room temperature, followed by the dropwise addition of a solution of 81.3 g. (0.6 mol) of β-diethyl amino ethyl chloride in 100 ml. of anhydrous toluene, and then by heating for 2 hours to boiling point. After the reaction solution had cooled, water was added to it, followed by working up in the same way as in Example 3. The compound in question was isolated in the form of its hydrochloride.

Hydrochloride: 123° – 125° C. (from ethyl acetate).

EXAMPLE 5

N,N-Diethyl-N-{2-[α-(tricyclo-(2.2.1.0$^{2,6}$)hept-3-ylidene)-benzyloxy]-ethyl}-amine 18 g. (0.6 mol) of sodium hydride (80% in mineral oil) and 250 ml. of dimethyl sulphoxide were heated with stirring for 1.5 hours at 70° C. until the evolution of hydrogen was over. After cooling to room temperature, a solution of 99.2 g. (0.5 mol) of tricyclo-(2.2.1.0$^{2,6}$)hept-3-yl phenyl ketone in 150 ml. of dimethyl sulphoxide was added and stirring continued for another hour during which the temperature rose to 50° – 55° C. A solution of 81.3 g. (0.6 mol) of β-diethyl amino ethyl chloride in 100 ml. of dimethyl sulphoxide was then added dropwise, followed by heating for another hour to 75° C. after the exothermic reaction had abated and the reaction temperature risen to 70° C. After cooling to room temperature, the reaction mixture was diluted with water, the aqueous solution was extracted with ether, the ethereal phase was dried with anhydrous sodium sulphate, filtered and concentrated in vacuo. The residue was dissolved in a mixture of 55 g. of concentrated hydrochloric acid and 450 g. of ice water, purified twice with 200 ml. of ether and, finally, the aqueous solution extracted 3 times with 400 ml. of chloroform. The combined chloroform extracts were purified with 400 ml. of water, dried over anhydrous sodium sulphate and concentrated in vacuo. The residue was alkalized, purified and fractionated in aqueous solution in the same way as in Example 3.

Bp. 0.1: 140° – 145° C. Yield: 129.4 g. (87% of the theoretical). Hydrochloride: 123° – 126° C. (from ethyl acetate).

EXAMPLE 6

N,N-Diethyl-N-{2-[α-(tricyclo-(2.2.1.0$^{2,6}$)hept-3-ylidene)-benzyloxy]-ethyl}-amine 5.48 g. (0.114 mol) of a 50% sodium hydride/mineral oil dispersion were repeatedly washed with petroleum ether in a nitrogen atmosphere, decanted off from the solvent, dried in vacuo and 80 ml. of anhydrous dimethyl formamide added dropwise under nitrogen while stirring and cooling with ice. This was followed by stirring for 30 minutes at 0° C. A solution of 19.83 g. (0.1 mol) of tricyclo-(2.2.1.0$^{2,6}$)hept-3-yl phenyl ketone in 30 ml. of anhydrous dimethyl formamide was then added dropwise, the mixture stirred for 15 minutes and, finally, a solution of 15.1 g. (0.111 mol) of β-diethyl amino ethyl chloride in 40 ml. of anhydrous dimethyl formamide added to it. The reaction mixture was then stirred for 30 minutes at 0° C., for 15 hours at room temperature and then for 3 hours at 40° C., the solvent evaporated off in a high vacuum and 44 ml. of 2N HCl added to the residue while cooling with ice/common salt. The reaction solution was purified with a total of 150 ml. of ether, extracted three times with 70 ml. of chloroform, the combined chloroform extracts dried with anhydrous sodium sulphate and concentrated in vacuo. The basic enol ether accumulating in the form of its hydrochloride was crystallized with ether. Hydrochloride: Mp: 120° – 123° C. (from ethyl acetate).

EXAMPLE 7

N,N-Diethyl-N-{2-[α-(tricyclo-(2.2.1.0$^{2,6}$)hept-3-ylidene)-benzyloxy]-ethyl-}amine 5.48 g. (0.114 mol) of a 50% sodium hydride/mineral oil dispersion were purified as described in Example 6, followed by the addition under nitrogen while stirring and cooling with ice/common salt of 80 ml. of anhydrous N-methyl pyrrolidone and a solution of 19.83 g. (0.1 mol) of tricyclo-(2.2.1.0$^{2,6}$) hept-3-yl phenyl ketone in 25 ml. of anhydrous N-methyl pyrrolidone, and then by the dropwise addition of 15.1 g. (0.111 mol) of β-diethyl amino ethyl chloride in solution in 20 ml. of anhydrous N-methyl pyrrolidone. After stirring for 15 hours at room temperature and then for 7 hours at 45° C., the reaction solution was diluted with 600 ml. of water and the aqueous solution extracted with ether. The ether extracts were dried over anhydrous sodium sulphate, filtered and concentrated in vacuo. The theoretical quantity of 2N hydrochloric acid was then added to the residue of the crude base while cooling with ice, and the required hydrochloride isolated in the same way as described in Example 6.

Hydrochloride: Mp: 123° – 125° C. (from ethyl acetate). Yield: 25.8 g. (77.2% of the theoretical).

EXAMPLE 8

N,N-Diethyl-N-{2-[α-(tricyclo-(2.2.1.0$^{2,6}$)hept-3-ylidene)-benzyloxy]-ethyl}-amine A mixture of 15.71 g. (0.14 mol) of potassium tert.-butylate in 80 ml. of anhydrous dimethyl sulphoxide was heated for 1 hour to 70° C., cooled to room temperature and a solution of 19.83 g. (0.1 mol) of tricyclo-(2.2.1.0$^{2,6}$)hept-3-yl phenyl ketone in 25 ml. of anhydrous dimethyl sulphoxide added with stirring in a nitrogen atmosphere. After stirring for 1 hour at 40° C., a solution of 18.98 g. (0.14 mol) of β-diethyl amino ethyl chloride in 15 ml. of anhydrous dimethyl sulphoxide was added dropwise with continued stirring, the mixture stirred for another 15 minutes at room temperature and then for 4 hours at 55° C. and finally worked up in the same way as described in Example 5.

Bp. 0.1: 135° – 140° C. Hydrochloride: Mp. 121° – 124° C. (from ethyl acetate).

EXAMPLE 9

N,N-Diethyl-N-{2-[α-(tricyclo-(2.2.1.0$^{2.6}$)hept-3-ylidene)-benzyloxy]-ethyl}-amine A solution of 14 g. (53.6 mMol) of β-chloroethyl-{α-[tricyclo-(2.2.1.0$^{2.6}$)hept-3-ylidene]-benzyl}-ether and 20 g. (0.273 mol) of diethyl amine in 130 ml. of benzene was heated for 5 hours to 140° C. in a 0.5 liter autoclave. After cooling, the diethyl amine hydrochloride was filtered off under suction, benzene and diethyl amine distilled off in vacuo and the residue left subjected to acid-alkaline working up. The basic fraction was fractionated in vacuo.

Bp. 0.1: 140° – 145° C. Hydrochloride: Mp: 123° – 125° C. (from ethyl acetate).

EXAMPLE 10

N,N-Diethyl-N-{2-[α-(tricyclo-(2.2.1.0$^{2.6}$)hept-3-ylidene)-benzyloxy]-ethyl}-amine A solution of 39 g. (0.125 mol) of α-[tricyclo-(2.2.1.0$^{2.6}$)hept-3-ylidene]-benzyloxy acetic acid-N,N-diethyl amide in 300 ml. of anhydrous ether was added dropwise to a suspension of 7.1 g. (0.187 mol) of lithium aluminium hydride in 100 ml. of anhydrous ether. On completion of the reaction, the reaction product was decomposed with water, followed by filtration under suction. The ethereal phase was concentrated by evaporation in vacuo. The oily residue left was fractionated in a high vacuum.

Bp: 0.05: 132° – 136° C. Yield: 30 g. (80.6% of the theoretical). Hydrochloride: Mp.: 121° – 123° C. (from ethyl acetate).

EXAMPLE 11

N,N-Diethyl-N-{2-[α-(tricyclo-(2.2.1.0$^{2.6}$)hept-3-ylidene)-benzyloxy]-ethyl}-amine A solution of 7.9 g. (34.9 mMol) of ethyl-{α-[tricyclo-2.2.1.0$^{2.6}$)-hept-3-ylidene]-benzyl}-ether and 21.4 g. (0.182 mol) of β-diethyl amino ethanol in 35 ml. of anhydrous chloroform was adjusted to pH 3.5° – 4 with concentrated hydrochloride acid. After stirring for 5 days at room temperature, another 3 drops of concentrated hydrochloric acid were added, the reaction mixture concentrated after 24 hours at room temperature, the residue taken up in water, extracted with petroleum ether and finally with chloroform. The chloroform phase was washed with a little water, dried with anhydrous sodium sulphate, filtered, concentrated in vacuo and crystallized with petroleum ether.

Hydrochloride: Mp.: 118° – 120° C.

N,N-Diethyl-N-{2-[α-(tricyclo-(2.2.1.0$^{2.6}$)hept-3-ylidene)-p-hydroxy benzyloxy]-ethyl}-amine was prepared by the same method and characterized by thin layer chromatography through the Rf-value 0.796 on silica gel in the eluent benzene : ethanol : concentrated ammonia (65 : 30 : 5).

EXAMPLE 12

N,N-Diethyl-N-{2-[α-(tricyclo-(2.2.1.0$^{2.6}$)hept-3-ylidene)-benzyloxy]-ethyl}-amine A solution of 4.5 g. (18.4 mMol) of tricyclo-(2.2.1.0$^{2.6}$)-hept-3-yl phenyl ketone dimethyl acetal in 7 ml. of methylene chloride and 4 drops of ethereal hydrochloric acid (100 mg. of HCl/ml.) in 1 ml. of methylene chloride were added dropwise with stirring over a period of 5 minutes at 55° C. to a solution of 2.83 g. (18.4 mMol) of β-diethyl amino ethanol hydrochloride in 35 ml. of anhydrous methylene chloride. The reaction mixture is immediately concentrated in vacuo, evaporated three times with 1 ml. of water, taken up in a little water, the aqueous phase purified with ether and extracted with chloroform. The chloroform solution was concentrated and the residue crystallized with ether.

Hydrochloride: Mp.: 116° – 120° C.

EXAMPLE 13

N,N-Diethyl-N-{2-[α-(tricyclo-(2.2.1.0$^{2.6}$)hept-3-ylidene)-benzyloxy]-ethyl}-amine A suspension of 19.5 g. (0.5 mol) of sodium amide in 250 ml. of anhydrous toluene was heated to boiling point, followed by the dropwise addition with stirring of a solution of 112.15 g. (0.5 mol) of α-ethinyl-α-[tricyclo-(2.2.1.0$^{2.6}$)hept-3-yl]-benzyl alcohol and 67.7 g. (0.5 mol) of β-diethyl amino ethyl chloride in 450 ml. of anhydrous toluene. After stirring for 1 hour at reflux temperature, the reaction mixture was cooled to room temperature and 125 ml. of water added dropwise. The organic phase was then separated off, washed three times with 125 ml of water, dried over anhydrous sodium sulphate and concentrated in vacuo. The crude base left was purified in the same way as in Example 3.

Bp. 0.1: 140°–145° C. Yield: 124 g. (83.3% of the theoretical). Hydrochloride: 121°–123° C. (from ethyl acetate).

EXAMPLE 14

N-{2-[α-(Tricyclo-(2.2.1.0$^{2.6}$)hept-3-ylidene)-benzyloxy]-ethyl}-morpholine

A solution of 19.83 g. (0.1 mol) of tricyclo-(2.2.1.0$^{2.6}$)-hept-3-yl phenyl ketone in 45 ml. of anhydrous toluene was added while stirring and boiling to a suspension of 3.9 g. (0.1 mol) of sodium amide in 45 ml. of anhydrous toluene, followed by etherification with a solution of 14.96 g. (0.1 mol) of N-(2-chloroethyl)-morpholine in 45 ml. of anhydrous toluene in the same way as in Example 3.

Bp: 0.001: 160°–170° C. Yield: 26.2 g. (84.3% of the theoretical). Hydrochloride: 170°–173° C. (from ethyl acetate/isopropanol).

EXAMPLE 15

N-Methyl-2-{2[α-(tricyclo-(2.2.1.0$^{2.6}$)hept-3-ylidene)-benzyloxy]-ethyl}-pyrrolidine 5.28 g. (0.11 mol) of a 50% sodium hydride/mineral oil dispersion were purified as in Example 6, followed by the dropwise addition while stirring under nitrogen of 80 ml. of dimethyl sulphoxide. The reaction mixture was then heated for 30 minutes at 70°–80° C. until the evolution of hydrogen stopped, after which it was cooled to room temperature and a solution of 19.83 g. (0.1 mol) of tricyclo-(2.2.1.0$^{2.6}$)-hept-3-yl phenyl ketone in 25 ml. of dimethyl sulphoxide added dropwise to it. After stirring for another hour at 35°–40° C., 16.25 g. (0.11 mol) of N-methyl pyrrolidyl-2-ethyl chloride in 15 ml. of dimethyl sulphoxide were added and the mixture stirred for another 2.5 hours at 35° to 40° C. The reaction mixture was then poured into 300 ml. of water, the oil precipitated was extracted with ether and the ether phase dried with anhydrous sodium sulphate. Filtration and concentration of the solvent by evaporation in vacuo left an oily residue which was converted into the hydrochloride in chloroform with 2N hydrochloric acid.

Hydrochloride: Mp.: 183°–186° C. (from ethyl acetate/isopropanol).

Yield: 25.3 g. (73.1 % of the theoretical).

EXAMPLE 16

N,N-Dimethyl-N-{3-[α-(tricyclo-(2.2.1.0$^{2.6}$)hept-3-ylidene)-benzyloxy]-propyl}-amine A solution of 19.83 g. (0.1 mol) of tricyclo-(2.2.1.0$^{2.6}$)-hept-3-yl phenyl ketone in 45 ml. of anhydrous toluene was added while stirring and boiling to a suspension of 3.9 g. (0.1 mol) of sodium amide in 45 ml. of anhydrous toluene, followed by etherification as in Example 3 with a solution of 12.2 g. (0.1 mol) of γ-dimethyl amino propyl chloride in 50 ml of anhydrous toluene.

Bp. 0.005: 135°–142° C. Yield: 22.3 g. (79% of the theoretical). Hydrochloride: 145°–148° C. (from ethyl acetate/isopropanol).

EXAMPLE 17

N,N-Diethyl-N-{3-[α-(tricyclo-(2.2.1.0$^{2.6}$)hept-3-ylidene)-benzyloxy]-propyl}-amine A mixture of 90 g. (0.327 mol) of γ-chloropropyl-{α-[tricyclo-(2.2.1.0$^{2.6}$)hept-3-ylidene]-benzyl}-ether, 96 g. (1.31 mol) of diethyl amine and 250 ml. of benzene, was heated for 4 hours to 160° C. in a 1 liter autoclave. After cooling, the diethyl amine hydrochloride was filtered off under suction, benzene and diethyl amine distilled off in vacuo and the residue left subject to acid-alkaline working up. The basic fraction was dried in ethereal phase over anhydrous sodium sulphate, filtered, concentrated and fractionated in vacuo.

Bp. 0.01: 135°–140° C. Yield: 72 g. (70.7% of the theoretical). Hydrochloride: Mp.: 104°–110° C. (from ethyl acetate).

EXAMPLE 18

N,N-Diethyl-N-{2-[α-(tricyclo-(2.2.1.0$^{2.6}$)hept-3-ylidene)-o-methyl benzyloxy]-ethyl}-amine A suspension of 16.77 g. (0.43 mol) of sodium amide in 195 ml. of anhydrous toluene was heated to boiling point, followed by the dropwise addition with stirring of a solution, of 91.3 g. (0.43 mol) of tricyclo-(2.2.1.0$^{2.6}$)hept-3-yl-o-tolyl ketone and 58.3 g. (0.43 mol) of β-diethyl amino ethyl chloride in 370 ml. of anhydrous toluene. After stirring for 3.5 hours at reflux temperature, the mixture was cooled to room temperature and 130 ml. of water added to destroy the sodium amide. The organic phase was separated off and purified, subjected to acid-alkaline working up and fractionated in a high vacuum in the same way as in Example 3.

Bp. 0.04: 136°–144° C. Yield: 95.1 g. (71% of the theoretical). Hydrochloride: 153°–155° C. (from ethyl acetate).

EXAMPLE 19

N,N-Diethyl-N-{2-[α-(tricyclo-(2.2.1.0$^{2.6}$)hept-3-ylidene)-p-methyl benzyloxy]-ethyl}-amine A solution of 21.23 g. (0.1 mol) of tricyclo-(2.2.1.0$^{2.6}$)-hept-3-yl-p-tolyl ketone in 45 ml. of anhydrous toluene was added while stirring and boiling to a suspension of 3.9 g. (0.1 mol) of sodium amide in 45 ml. of anhydrous toluene followed by etherification as in Example 3 with a solution of 13.56 g. (0.1 mol) of β-diethyl amino ethyl chloride in 45 ml.of anhydrous toluene.

Bp. 0.002: 129°–136° C. Hydrohloride: 146°–148° C. (from ethyl acetate).

EXAMPLE 20

N,N-Diethyl-N-{2-[α-(tricyclo-(2.2.1.0$^{2.6}$)hept-3-ylidene)-m-chlorobenzyloxy]-ethyl}-amine A solution of 23.3 g. (0.1 mol) of tricyclo-(2.2.1.0$^{2.6}$)-hept-3-yl-m-chlorophenyl ketone in 45 ml. of anhydrous toluene was added while stirring and boiling to a suspension of 3.9 g. (0.1 mol) of sodium amide in 45 ml. of anhydrous toluene, followed by etherification as in Example 3 with 13.56 g. (0.1 mol) of β-diethylamino ethyl chloride in 45 ml. of anhydrous toluene. The reaction product was worked up in the same way as in Example 3, the crude base obtained was purified through an aluminium oxide column and fractionated.

Bp. 0.07: 158°–164° C. Yield: 23.6 g. (71.1% of the theoretical). Hydrochloride: 110°–114° C. (from benzene/petroleum ether).

EXAMPLE 21

N,N-Diethyl-N-{2-[α-(tricyclo-(2.2.1.0$^{2.6}$)hept-3-ylidene)-p-chlorobenzyloxy]-ethyl}-amine A solution of 23.3 g. (0.1 mol) of tricyclo-(2.2.1.0$^{2.6}$)-hept-3-yl-p-chlorophenyl ketone in 45 ml. of anhydrous toluene was added while stirring and boiling to a suspension of 3.9 g. (0.1 mol) of sodium amide in 45 ml. of anhydrous toluene, followed by etherification as in Example 3 with a solution of 13.56 g. (0.1 mol) of β-diethyl amino ethyl chloride in 45 ml. of anhydrous toluene.

Bp. 0.01: 150°–157° C. Yield: 24.2 g. (73% of the theoretical).

Hydrochloride: 112°–114° C. (from ethyl acetate).

EXAMPLE 22

N,N-Diethyl-N-{2-[1-(2-pyridyl)-1-(tricyclo-(2.2.1.0$^{2.6}$)hept-3-ylidene)-methoxy]-ethyl}-amine 2.57 g. (53.6 mMol) of a 50% sodium hydride/mineral oil dispersion were purified in the same way as in Example 6, followed by the dropwise addition while stirring under nitrogen of 40 ml. of dimethyl sulphoxide. The reaction mixture was then heated for 30 minutes at 70° to 80° C. until the evolution of hydrogen was over, cooled to room temperature, a solution of 9.7 g. (48.7 mMol) of tricyclo-(2.2.1.0$^{2.6}$)hept-3-yl-(2-pyridyl)-ketone in 10 ml. of dimethyl sulphoxide added dropwise, the mixture stirred for another at 35 to 40° C., 7.27 g. (53.6 mMol) of β-diethyl amino ethyl chloride in 10 ml. of dimethyl sulphoxide added and the mixture stirred for another hour at 35 to 40° C. The reaction mixture was then diluted with 300 ml. of water, extracted with ether and the ether phase dried with anhydrous sodium sulphate. Filtration and concentration of the ethereal solution by evaporation in vacuo left an oily residue which was purified through an aluminum oxide column and converted into the monohydrochloride of the required compound in the usual way with ethereal hydrochloric acid.

Monohydrochloride: Mp.: 132°–135° C.

EXAMPLE 23

N,N-Diethyl-N-{2-[1-(4-pyridyl)-1-(tricyclo-(2.2.1.0$^{2.6}$)hept-3-ylidene)-methoxy]-ethyl}-amine A solution of 17.87 g. (89.6 mMol) of tricyclo-(2.2.1.0$^{2.6}$)-hept-3-yl-(4-pyridyl)-ketone in anhydrous toluene was added while stirring and boiling to a suspension of 3.5 g. (89.7 mMol) of sodium amide in 45 ml. of anhydrous toluene, followed by etherification for 2 hours as in Example 3 with 12.16 g. (89.7 mMol) of β-diethyl amino ethyl chloride in anhydrous toluene.

The crude base obtained by working up the reaction mixture in accordance with Example 3 was suspended in water, followed by the dropwise addition while cooling with ice of a solution of 8.83 g. of concentrated hydrochloric acid in 20 ml. of ice water. After extraction with a total of 100 ml. of ether, the aqueous phase is separated off and alkalized while cooling with a solution of 8.95 ml. of 10N sodium hydroxide in 20 ml. of water. The base precipitated was extracted with ether, the ether phase dried, concentrated and fractionated.

The hydrochloride was synthesized while cooling with ice by adding 2N hydrochloric acid to a solution of the base in chloroform, briefly extracting the organic phase by shaking with a little water, drying the chloroform solution with anhydrous sodium sulphate, concentrating the solvent by evaporation and rubbing with ether.

Monohydrochloride: Mp.: 122°–125° C.

EXAMPLE 24

N,N-Diethyl-N-{2-[α-(tricyclo-(2.2.1.0$^{2.6}$)hept-3-ylidene)-2-thienyloxy]-ethyl}-amine A mixture of 3.8 g. (79.1 mMol) of 50% sodium hydride dispersion (purified as in Example 6) in 80 ml. of dimethyl sulphoxide was heated for 1 hour at 70 — 80° C. until the evolution of hydrogen was over, a solution of 16 g. (78.2 mMol) of tricyclo-2.2.1.0$^{2.6}$)hept-3-yl-(2-thienyl)-ketone in 25 ml. of dimethyl sulphoxide added dropwise while stirring under nitrogen at room temperature, the reaction mixture stirred for 1 hour at room temperature and etherified in accordance with Example 5 with 10.7 g. (79.1 mMol) of β-diethyl amino ethyl chloride in 14 ml. of dimethyl sulphoxide for 1 hour at 50°–60° C. and then for 15 hours at room temperature. After working up as in Example 5, the crude base was purified to the stage of its hydrochloride, purification of the base liberated was completed by separation through an aluminium oxide column, followed finally by characterisation again in the form of the hydrochloride.

Hydrochloride: Mp.: 141°–144° C.

EXAMPLE 25

| Coated tablets | |
|---|---|
| | 1 kernel contains: |
| N,N-Diethyl-N-{2-[α-(tricyclo-(2.2.1.0$^{2.6}$)hept-3-ylidene)-benzyloxy]-ethyl}-amine-hydrochloride (corresponds to 10 mg. of the base compound) | 11.223 mg. |
| polyvinylpyrrolidone (product Kollidon 25 of BASF) | 0.225 mg. |
| corn starch | 49.400 mg. |
| lactose | 37.100 mg. |
| sec. calcium phosphate, anhydrous | 35.200 mg. |

EXAMPLE 25-continued

| Coated tablets | |
|---|---|
| | 1 kernel contains: |
| gelatine | 1.852 mg. |
| talcum | 4.000 mg. |
| magnesium stearate | 1.000 mg. |
| | 140.000 mg. |

The corn starch, lactose and calcium phosphate are passed through a 1 mm. sieve, are homogeneously mixed and are moistened with a 4% aqueous solution of the gelatine. The resulting mixture is passed through a 2 mm. sieve and dried until a relative humidity of 45% (measured by means of a sample hygrometer). The resulting product and the active compound, talcum and magnesium stearate are passed through a 0.75 mm. sieve and thereafter are homogeneously mixed. The product which now is ready for pressing, is pressed to kernels having a diameter of 7 mm., a camber radius of 5 mm. and a weight of 140 mg. each. The kernels are checked in a control laboratory for mistakes. Thereafter, they are coated in a usual way with 5 mg. of a coating consisting of an acrylic methacrylic ester copolymer, softening agents and colour pigments.

EXAMPLE 26

| Suppositories | |
|---|---|
| | 1 suppository contains: |
| N,N-Diethyl-N-{2-[α-(tricyclo-(2.2.1.0$^{2.6}$)hept-3-ylidene)-benzyloxy]-ethyl}-amine-hydrochloride (corresponds to 20 mg. of the base compound) | 22.446 mg. |
| hardened fat DAB 7 | 1.977.554 mg. |
| | 2.000.000 mg. |

The active compound is sieved to a particle size of 75 micrometers. It is slowly poured into the molten fat at 40° C. with thorough stirring and thus homogeneously mixed. The mixture is formed into suppositories weighing 2 g. each by means of molds or PVC film multiple molds.

EXAMPLE 27

| Injection solutions | |
|---|---|
| | 2 cc. contain: |
| N,N-Diethyl-N-{2-[α-tricyclo-(2.2.1.0$^{2.6}$)hept-3-ylidene)-benzyloxy]-ethyl}-amine | 10.000 mg. |
| sodium dihydrogen phosphate × 2 H$_2$O | 11.544 mg. |
| sodium monohydrogen phosphate × 12 H$_2$O | 45.120 mg. |
| ethanol | 0.200 cc. |
| emulgator (ethoxylated castor oil, product Cremophor EL of BASF) | 40.000 mg. |
| aqua pro injectione, upt to a total volume of | 2.000 cc. |

The active compound is dissolved in a mixture of the ethanol and the emulgator and the resulting solution is poured into the solution of the phosphates in the water with stirring. The resulting solution is filtered through a steril Seitz-EKS-filter under aseptic conditions and under nitrogen and then is filled into ampoules of brown glas of 2.15 cc. each under aseptic conditions and under nitrogen.

What we claim is:

1. A compound selected from the group consisting of the basic enol ethers having the formula I

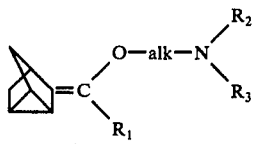

(I)

wherein $R_1$ represents a member selected from the group consisting of the unsubstituted phenyl group and the phenyl group substituted by members selected from the group consisting of halogen, lower alkyl having from 1 to 4 carbon atoms, nitro, trifluoromethyl, hydroxy and lower alkoxy having from 1 to 4 carbon atoms, alk is a member selected from the group consisting of the linear and branched alkylene groups having from 2 to 4 carbon atoms, and $R_2$ and $R_3$, which may be the same or different, represent members selected from the group consisting of hydrogen and alkyl having 1 to 4 carbon atoms, and the pharmacologically acceptable acid addition salts.

2. A compound as claimed in claim 1, wherein $R_1$ represents a member selected from the group consisting of the phenyl group and the phenyl group monosubstituted in the ortho position by a member selected from the group consisting of bromine, chlorine, fluorine, lower alkyl having from 1 to 4 carbon atoms, nitro, trifluoromethyl, hydroxy and lower alkoxy having from 1 to 4 carbon atoms, alk is the ethylene group and both $R_2$ and $R_3$ represent the ethyl group.

3. A compound selected from the group consisting of N,N-diethyl-N-{2-[α-(tricyclo-(2.2.1.0$^{2.6}$)hept-3-ylidene)-benzyloxy]-ethyl}-amine and its pharmacologically acceptable acid addition salts.

4. A compound selected from the group consisting of N,N-diethyl-N-{2-[α-(tricyclo-(2.2.1.0$^{2.6}$)hept-3-ylidene)-o-methyl-benzyloxy]-ethyl}-amine and its pharmacologically acceptable acid addition salts.

* * * * *